United States Patent [19]

See et al.

[11] Patent Number: 4,955,878

[45] Date of Patent: Sep. 11, 1990

[54] KIT FOR PREVENTING OR TREATING ARTERIAL DYSFUNCTION RESULTING FROM ANGIOPLASTY PROCEDURES

[75] Inventors: Jackie R. See, Fullerton; William E. Shell, Los Angeles, both of Calif.

[73] Assignee: Biotechnology, Inc., Los Angeles, Calif.

[21] Appl. No.: 281,430

[22] Filed: Dec. 8, 1988

Related U.S. Application Data

[63] Continuation-in-part of Ser. No. 848,233, Apr. 4, 1986, Pat. No. 4,820,732, which is a continuation-in-part of Ser. No. 784,160, Oct. 4, 1985, abandoned.

[51] Int. Cl.$^5$ ............................................. A61M 5/00
[52] U.S. Cl. ..................................... 604/181; 514/573
[58] Field of Search ........................... 604/181, 48, 50; 514/573; 600/1, 3, 4

[56] References Cited

U.S. PATENT DOCUMENTS

| | | | |
|---|---|---|---|
| 3,966,962 | 6/1976 | Yalkowsky | 424/305 |
| 4,095,036 | 6/1978 | Yankee | 560/121 |
| 4,103,026 | 7/1978 | Carlson | 424/305 |
| 4,205,178 | 5/1980 | Axen | 560/121 |
| 4,239,778 | 12/1980 | Venton et al. | 424/305 |
| 4,558,037 | 12/1985 | Chan et al. | 514/20 |
| 4,734,424 | 3/1988 | Hall et al. | 514/382 |

OTHER PUBLICATIONS

Cragg, A. et al., "Vessel Wall Arachidonate Metabolism After Angioplasty: Possible Mediators of Postangioplasty Vasospasm", American Journal of Cardiology, vol. 51, pp. 1441-1445, (5-1-83).
Zollikofer, C. L. et al., "Interventional Radiology--Prostaglandins and Angioplasty", Radiology, vol. 149, No. 3, pp. 681-685, Dec. 1983.
Faxon et al., "Effect of Antiplatelet Therapy on Restenosis After Experimental Angioplasty", American Journal of Cardiology, vol. 53, pp. 72C-76C, (6-15-84-/Suppls.).

*Primary Examiner*—C. Fred Rosenbaum
*Assistant Examiner*—Mark O. Polatta
*Attorney, Agent, or Firm*—Donald L. Corneglio

[57] ABSTRACT

A kit for preventing or treating arterial dysfunction resulting from an angioplasty procedure and particularly, in myocardial angioplasty procedures in human beings. The kit provides the materials necessary to introduce a selected amount of an intraarterial prostaglandin compound into an artery, such as a coronary artery, in which an angioplasty procedure is to occur and an intravenous prostaglandin compound. The prostaglandin compound will provide cyto-protection and provide antithrombotic effects and antiplatelet effects and antispasmatic effects. A composition is also provided for reducing dysfunction in angioplasty procedures and comprises a selected amount of a carrier and a prostaglandin compound carried in a specified amount and which carrier does not alter the prostaglandin compound and releases the prostaglandin compound at a rate sufficient to dilate blood vessels to thereby produce the required efficacy. The kit is a prepackaged combination of components which provides for the complete administration of the prostaglandin compound before, during and after the angioplasty procedure.

15 Claims, No Drawings

KIT FOR PREVENTING OR TREATING ARTERIAL DYSFUNCTION RESULTING FROM ANGIOPLASTY PROCEDURES

CROSS REFERENCE TO RELATED APPLICATIONS

This application is a continuation-in-part of U.S. Ser. No. 848,233, filed 4 Apr. 1986 now U.S. Pat. No. 4,820,732 which was a of U.S. Ser. No. 784,160, filed 4 October 1985, abandoned.

BACKGROUND OF THE INVENTION

This invention relates in general to certain new and useful improvements in methods for reducing dysfunction in angioplasty procedures, and more particularly, to a kit which provides all components for the introduction of a selected amount of a prostaglandin compound into the artery in which an angioplasty procedure is performed and compositions containing specified amounts of the prostaglandin compound to produce a high degree of efficacy.

Angioplasty procedures were first used in the 1960's and since that time have gained widespread acceptance as a means of obtaining dilation of arteries. Particularly, angiomyocardial angioplasty procedures have become widely adopted to obtain dilation of myocardial arteries.

In the conventional angioplasty procedure, a small balloon tipped catheter is introduced into an artery, often using a guide wire to a catheter tube in which a balloon may be positioned at an artery stenosis. These balloons and catheter assemblies are often referred to as coronary balloon dilation catheters. In many cases, the catheters are designed to permit continued distal dye injections through the balloon to permit visual verification of proper approach to a lesion or other area in which the procedure is to be employed.

It is well known that cardiac angioplasty procedures involve a risk of both local and systemic thromboembolic effects, which are even greater than cardiac catheterization. Usually, the patient is injected with heparin and various known blockers during the procedure. Moreover, for a substantial period of time after the procedure, which may be six months to a year, or longer, the patient must necessarily be treated with platelet inhibiting drugs. Other complications which often occur during transluminal angioplasty procedures include dissection of an artery such as a coronary artery, intramural hematoma and occlusion of the artery resulting in myocardial infarction.

Some of the problems which appear to arise after angioplasty procedures include early restenosis and possibly abrupt occlusion. It is therefore necessary to provide some means which exhibits a cytoprotective effect during ischemia and which may salvage the myocardium during transluminal angioplasty, particularly when high inflation pressures are needed for a long duration, as for example, up to six minutes, or otherwise, in the case of an unstable angina.

In order to overcome some of the dysfunction resulting from percutaneous transluminal coronary angioplasty, heparin and intracoronary nitroglycerine, as well as systemic calcium blockers have been used. In addition, various preparations have been employed prior to the angioplasty procedures and include, for example, aspirin, Persantine, intravenous dextran, etc. Nevertheless, the various complications still persist. Moreover, these complications account for virtually all of the problems in percutaneous transluminal coronary angioplasty. In the NHLBI registery, as reported by Cowley, et al., in the American Journal of Cardiology, 1984, the results of the cases of 3,079 patients were examined and 418 patients suffered some form of post angioplasty procedure complications.

INFORMATION DISCLOSURE

There have been numerous publications dealing with the various types of prostaglandin compounds and their effectiveness for providing antiplatelet effects and antithrombotic effects and antispasmic effects. For example, U.S. Pat. No. 3,966,962 to Yalkowsky or U.S. Pat. No. 4.239,778 to Venton, et al. which discloses a novel azaprostanoic acid analog and its effectiveness as an inhibitor of platelet aggregation. U.S. Pat. No. 4,095,036 to Yankee discloses an 8-beta 12-alpha PG-2 prostaglandin type analog and its effectiveness in controlling spasm, particularly in asthmatic conditions, as well as a decrease in blood platelet adhesiveness. This patent also discloses the use of various prostaglandin analogs as being effective to prevent the formation of thrombi to thereby prevent post operative thrombosis and their effectiveness in and prevention of myocardial infarcts. Also, U.S. Pat. No. 4,103,026 to Carlson discloses the treatment of peripheral vascular disease by non-arterial administration of prostaglandin El.

In like manner, U.S. Pat. No. 4,205,178 to Axon discloses various prostaglandin E derivatives and analog compounds which are also effective in prevention of myocardial infarcts and effective in inhibiting platelet aggregation. This patent also discloses the use of these compounds as hypotensive agents when administered at a rate of about 0.01 to about 50 micrograms per kilogram of body weight per minute.

There have been several articles dealing with the effects of prostaglandin reduction as a result of arterial insult. For example, the article entitled "Vessel Wall Arachidonate Metabolism After Angioplasty" by Andrew Cragg. M.D., et al., discusses the mechanism of post angioplasty vasospasm and the postulation that a reduction in prostaglandin I-2 or prostaglandin E-2 might contribute to spasm of a dilated artery, as reported in the May 1, 1983 edition of the American Journal of Cardiology, Vol. 51, pages 1441 et seq. In like manner, a discussion of paralysis and hyperemia of an arterial wall and altered vasomotor tone has been demonstrated following percutaneous transluminal angioplasty and the effect of reduction of prostaglandin compounds generated by the body, in "Prostaglandins and Angioplasty" as reported in Interventional Radiology, December 1983, page 681 et seq.

Faxon et al., Effect of Antiplatelet Therapy on Restenosis After Experimental Angioplasty, Am J Cardiol 53:72C.76C (1984) disclosed aspirin to be effective as an antiplatelet drug useful in the prevention of restenosis after angioplasty. Cragg et al., Vessel Wall Arachidonate Metaboism After Angioplasty, Am J Cardiol 51:1441-45 (1983) reported that occulsion after angioplasty appears to be related, among other things, to a reduction in prostaglandin.

SUMMARY OF THE INVENTION

The present invention provides a means for preventing or treating arterial dysfunction in an angioplasty procedure, by administering to a patient, a pharmacological amount of a composition which will provide antiplatelet effects, antispasmatic effects and probable antithrombotic effects. The present invention reduces the dysfunction which can arise in or from an angioplasty procedure by administering to a patient a prostaglandin E-1 composition, both during the angioplasty procedure and intravenously for a selected time period thereafter.

In yet another aspect, the present invention provides a means of reducing dysfunction which may arise in an angioplasty procedure by administering to an intracoronary artery of the patient an amount of a prostaglandin compound substantially in excess of the amount which would have been generated by a normal myocardial artery when insulted, such that the amount of prostaglandin compound administered is substantially greater than an amount which would be administered in a replacement therapy. The present invention provides a composition for reducing the dysfunction which can normally arise in an angioplasty procedure and which comprises a selected carrier containing a specified amount of a prostaglandin compound to produce the desired efficacy.

The present invention is a pre-packaged combination of components which is effective for reducing dysfunction in an angioplasty procedure. The kit contains a combination of components for preventing or treating arterial dysfunction resulting from angioplasty procedures. Generally, the kit contains a first container comprising about 25 to about 200 nanograms of a prostaglandin $E_1$ or a prostaglandin pharmacologically equivalent thereto for bolus injection into an artery of a patient; a second container comprising a prostaglandin $E_1$ or a prostaglandin pharmacologically equivalent thereto for intravenous administration after said bolus injection sufficient to provide 10 to about 100 nanograms per kilogram of body weight per minute over at least a 6 hour period; a chart cross-referencing an amount of said prostaglandin from said second container to body weights to be admixed with a saline solution to prepare a dosage amount of about 10 nanograms to about 100 nanograms per kilogram of body weight per minute.

The kit can additionally include a sealed package of saline solution for preparing the intravenous administration. The first and/or second container can be syringes containing the prostaglandin. Preferably, the first container contains about 40 to about 130 nanograms of said prostaglandin or about 65 nanograms of the prostaglandin in a 1 cc solution. The kit can additionally include a third container comprising about 25 to about 200 nanograms of the prostaglandin for injection into the artery after an angioplasty procedure. Preferably, the third container contains about 40 to about 130 nanograms of the prostaglandin or about 65 nanograms of the prostaglandin in a 1 cc solution.

The kit can also be assembled such that the second container is a container of saline solution containing an amount of the prostaglandin to provide a 15 to about 40 nanograms of prostaglandin per kilogram of body weight per minute. Preferably, the prostaglandin in each of the containers is present in a carrier comprising (a) an isotonic solution, (b) an angiographic contrast material, (c) a biodegradable prostaglandin carrying microsphere or (d) a combination thereof. The microspheres may comprise albumen laden microspheres, carbohydrate laden microspheres or free fatty acid laden microspheres. Preferably, the carrier comprises an isotonic solution which is present in a 5 cc amount; an angiographic contrast material present in an amount of about 3 cc to about 10 cc per bolus; or biodegradable rostaglandin carrying microspheres having sizes within the range of about 10 microns to about 100 microns and which are present in an amount of about 225,000 to about 500,000.

DETAILED DESCRIPTION OF THE INVENTION

The present invention relies on a discovery that it is possible to substantially reduce dysfunction in angioplasty procedures in human beings, by introduction in relations to an artery in which an angioplasty procedure is to occur, a selected amount of intraarterial prostaglandin compound. This prostaglandin compound is administered in a proper amount which will provide cyto-protection and provide antithrombotic effects, antiplatelet effects and antispasmic effects.

The prostaglandin compound may adopt the form of several well known prostaglandin analogs and isomers, as hereinafter described, and include, for example, the prostaglandin E compounds, the prostaglandin I compounds, the prostaglandin D compounds, the prostaglandin F compounds. Ciprostene, etc. Some of the more preferred prostaglandin compounds used in accordance with the present invention include, prostaglandin E-1, prostaglandin I.2 and Ciprostene.

Generally, the prostaglandin compound may be administered before the angioplasty procedure, during the angioplasty procedure and in many cases, it is administered for a selected time period thereafter. In the case of a coronary angioplasty procedure, an intracoronary bolus injection is administered, followed by a continuous intravenous injection for a selected time period, as for example, 6 to 12 hours or more. More preferably, an intracoronary prostaglandin bolus injection is administered immediately prior to the procedure and another intracoronary prostaglandin bolus injection is administered immediately after the procedure, and which is followed by the intravenous administration. Intracoronary prostaglandin administration during the procedure may also take place, as required.

The prostaglandin compound may be dissolved in a liquid carrier, as for example, a dehydrated alcohol. However, other liquid carriers, hereafter specified may be used. The liquid carrier must be pharmaceutically acceptable and pharmacologically inactive.

It is well known that the normal body artery will generate one or more of the selected prostaglandin compounds, as for example, prostaglandin I-2 when the artery is insulted, that is stressed or otherwise subjected to an injury. See, for example, "Vessel Wall Archiondonate Metabolism After Angioplasty" by Andrew Cragg, M.D., et al., supra. See also. "The Treatment of Vasospastic Disease With Prostaglandin D.1", British medical Journal, Vol. 201. In a typical myocardial insult, the myocardial artery will generate prostaglandin usually in an amount of about one picogram up to a maximum of about three picograms. See, for example, "Vascular Prostaglandin and Thromboxane Production in a Canine Model of Myocardial Ischemia" by James M. Schmitz, et al., Circulation Research, Vol. 57, No. 2, August 1985; "Prostaglandins in Cardiovascular Medicine: Part 1", by John G. Harold, M.D., William E. Shell, M.D., et al.; "Gardiovascular Reviews and Reports", Vol. 5, No. 9, September 1984.

The amount of prostaglandin compound which is administered in accordance with the present invention will range depending on the condition of the patient, including his or her health, age, previous coronary history, ability to accept the prostaglandin without adverse side effects and like factors. Generally, in a coronary angioplasty procedure the amount of intracoronary prostaglandin administered to a patient ranges from about 25 nanograms to about 400 nanograms in bolus administrations and preferably ranges from about 80 nanograms to about 260 nanograms, based on prostaglandin E-1. The amounts of intracoronary prostaglandin which are administered represent generally the total amount immediately prior to, during and immediately after the angioplasty procedure. Thus, the first bolus injection may comprise about 12 to about 200 nanograms, and preferably about 40 to about 130 nanograms. The second or post-procedure bolus injection may also comprise about 12 to about 200 nanograms and preferably about 40 to about 130 nanograms.

More preferably, about 65 nanograms of prostaglandin is administered immediately prior to the angioplasty procedure and an additional amount of about 65 nanograms of prostaglandin is administered immediately after the angioplasty procedure in bolus injections, based on prostaglandin E-1. If the prostaglandin compound is administered during the angioplasty procedure, the amounts administered immediately prior to and/or immediately after the procedure can be altered so that the total amount administered falls within the above specified ranges.

The above ranges and specific amounts identified are those specifically for prostaglandin E-1. The ranges for the other prostaglandin analogs and isomers encompassed by the present invention and the specific amounts therefore are based on the efficacy of such isomers or analogs compared to prostaglandin E-1. Thus, for example, if a particular prostaglandin compound encompassed by the present invention has an efficacy of about 50 percent that of prostaglandin E-1, the ranges and the specific amounts administered of that compound would be doubled.

Inasmuch as the prostaglandin compounds are administered in accordance with the present invention in nanogram amounts (1-billionth of a gram) and at minimum, 25 nanograms, and the amount of prostaglandin which may be generated by any body artery on insult is no greater than picogram amounts (1 trillionth of a gram) and usually less than 3 picograms, it can be seen that the prostaglandin compounds administered in accordance with the present invention are administered in amounts almost one thousand times, and usually much greater than one thousand times the amount of prostaglandin which could be generated by any normal body artery when insulted. Thus, the administration of prostaglandin compounds in the nanogram range as specified herein constituted a pharmacological amount and does not merely operate as a replacement, as for example, in replacement therapy, that is, administration of an amount to replace that which may have been lost. As an example, cortisone may be administered when body cortisone generation is depleted, although in amounts massively greater than the amounts depleted and is thus considered to be a pharmacological administration.

In view of the above explanation of administered prostaglandin amounts, the term "pharmacological amount" is used herein to mean the administration of the prostaglandin compound in an amount substantially greater than the amount of prostaglandin which would be generated by a myocardial artery when insulted, and usually in an amount of about at least one thousand times greater than the amount which would be generated by a normal myocardial artery when insulted.

The administration of the prostaglandin compound in the pharmacological amount produces unexpected results in that the coronary artery or other artery in which the prostaglandin was administered remains dilated for a period of two to three times longer than if nitroglycerine or verapamil or both were administered. Moreover, the amount of arterial dilation is substantially greater and in many cases, the duct of the artery will remain dilated to twice its original size. As an example, in an angioplasty procedure, the artery may remain dilated for a period of about 45 seconds after removal of the catheter tip. With administration of nitroglycerine, the artery may remain dilated for a period of about two minutes. With the administration of prostaglandin E-1, the same artery will remain dilated for a period of seven minutes or longer. This dilation period enables the body to overcome the results of abrupt occlusion or other dysfunction which often results after an angioplasty procedure. In addition, there is a substantially greater length of the myocardial artery which is dilated after the administration of the prostaglandin compound in the pharmacological amount. For example, a length of artery which is dilated may easily exceed two to three times the length of artery section which is dilated under the administration of nitroglycerine.

This invention process has many other advantages and has other purposes which may be made more clearly apparent from a consideration of the forms in which it may be embodied. These forms are set forth in the following detailed description. However, its to be understood that the detailed description is only for purposes of illustrating the general principles of the invention and that it is to be understood that such detailed description is not to be taken in a limiting sense.

In accordance with the present invention, a prostaglandin compound, as hereinafter described in more detail, is administered to the artery of a human being in which an angioplasty procedure is to occur. As indicated previously, this prostaglandin compound is administered in an amount required to provide cyto-protection, antithrombotic effects, antiplatelet effects and antispasmic effects.

Generally, the prostaglandin compound is administered in the region in which the balloon catheter is to be inserted in order to reduce the otherwise adverse side affects and dysfunctions which may result when attempting to dilate an artery. While the prostaglandin compound is generally administered just prior to the angioplasty procedure, in many cases it is desirable to administer the prostaglandin compound to the patient during the procedure and/or for some time period thereafter and which is hereinafter described in more detail.

The method of the present invention was developed and has been proved to be highly effective in myocardial angioplasty procedures. However, the method of the present invention utilizing the administration of the prostaglandin compound is also highly effective for conducting angioplasty procedures in other portions of the human body. Thus, and while the preferred embodiment of the invention deals with myocardial angioplasty procedures, it is to be understood that the invention is applicable to other angioplasty procedures as well.

Prostaglandin compounds which are used in accordance with the present invention are unsaturated fatty acids containing 20 carbon atoms and which usually include a pair of spaced apart side chains and each of which form somewhat of a saw-tooth configuration, much in the same form as a hair pin. The two side chains are joined at one end only, by means of a cyclopentane ring. At the other end, one of the side chains terminates in a carboxylic acid group. In addition, the two side chains may be provided with one or more hydroxyl groups and/or ketone groups along the length thereof. These prostaglandins generally have a chemical structure which may be diagrasmatically illustrated in the generalized structural formula I.

These prostaglandins, which are collectively often referred to as "eicosanoids", are known to exhibit biological activities. These activities include effects on the muscles of vessels, and/or inflammatory response, thermo-regulation, platelet aggregation and the like. However, heretofore, it has not been recognized that the Prostaglandin compound could be effective in reducing and even overcoming most of the dysfunction resulting from and in angioplasty procedures.

Prostaglandin E-1 is one of the preferred prostaglandin compounds which may be used in accordance with the method of the present invention. The prostaglandin E-1 compound is metabolically derived from the polyunsaturated fatty acid, dihomo-y-linolenic acid. This prostaglandin E-1, has the empirical formula $C_{20}H_{34}O_5$ and this prostaglandin E-1 compound has the chemical formula (11a,13E,15S)-11,15-dihydroxy-9-oxoprost-13-en-1-ox acid. Prostaglandin compounds of this type are more fully described in U.S. Pat. No. 3,069,322 to Bergstrom, et al.

Prostaglandin E-1 can be structurally diagramed as shown in structural formula II.

The dotted lines between carbon No. 7 and carbon No. 8 indicate orientation of the atom and any group attached thereto below the plane of the ring in the alpha stereochemistry. In other words, that orientation is below the plane of this paper. The same holds true with the hydroxyl groups at the No. 11 and No. 15 carbon atoms.

The prostaglandin used in accordance with the present invention is not limited to the prostaglandin E-1 compound but encompasses other derivatives of prostanoic acid and includes all other prostaglandins which provide the desired pharmacological effects such as cyto protection. Those prostaglandins include, for example, prostaglandin E-2 and prostaglandin E-3. The prostaglandin compounds are also deemed to include their lower alkyl esters and salts and amides which exhibit the desired pharmacological activity. The prostaglandin E-2 compounds are disclosed in U.S. Pat. No. 3,598,858 and esters thereof are disclosed in U.S. Pat. No. 3, 691,216 and U.S. Pat. No. 3,795,697.

The numerals following the designations "prostaglandin" or "prostaglandin E" e.g., "1", "2". "3", represent the total number of double bonds in the two side chains. Thus, prostaglandin E-2 has an additional double bond between carbon No. 5 and carbon No. 6 and has a structural formula as shown in formula III.

Prostaglandin E-3 has still an additional double bond between carbon No. 16 and carbon No. 17 and has a structural formula as shown in formula IV.

The compositions used in the method of the present invention also include the various isomers, as aforesaid, and include for example prostaglandin A isomers and the prostaglandin B isomers. The prostaglandin A compounds do not include the hydroxyl group at carbon No. 11, but have a double bond within the ring between carbon No. 10 and carbon No. 11. Thus, prostaglandin A-1 has a structural formula as shown in formula V.

The prostaglandin B compounds are isomers of the prostaglandin A compounds having a double bond between carbon No. 8 and carbon No. 12. Thus, prostaglandin B-1 has a structural formula as shown in formula VI.

The compound prostaglandin F is also, for example, encompassed by the present invention. The prostaglandin F compounds have a hydroxyl group at the No. 9 carbon atom in place of a ketone group. Thus, prostaglandin F-2α has a structural formula as shown in formula VII.

The prostaglandin compounds having the chemical name "Ciprostene", namely, 9-methylcarbacyclin-calcium salt and having the empirical formula $C_{20}H_{34}O_5$ are also prostaglandin compounds which are encompassed by and achieve the efficacious results in accordance with the present invention. The Ciprostene form of prostaglandin is usually characterized as a calcium salt and is a chemically stable analog of prostacyclin. Ciprostene has a structural formula as shown in formula VIII.

It can be observed that the above are a non-limiting list of the prostaglandins which can be used and show that essentially any prostaglandin which provides the desired pharmacological effect can be employed. Moreover, in a broad sense and considering the generalized structural formula set forth above, it should be understood that the orientation, as shown in dotted lines, may be in or out of the plane of the cyclopentane, that is in or out of the plane of this paper.

Thus, the prostaglandin compound encompassed by the present invention, as represented by the generalized formula set forth above, is comprised of a cyclopentane ring having a pair of side chains therein and one of which terminates with a COO-moiety. The "dotted" bond in the generalized structural formula may be in or out of the plane of the cyclopentane ring and any of the bonds in the side chains may be single bonded or double bonded and which may also be in or out of the plane of the side chains and which side chains may include hydroxyl and ketone moieties thereon which may be in or out of the plane of the cyclopentane ring.

The COO- group, which may be represented by COOR, is preferably a carboxylic acid group, e.g. COOH. However, the R may be hydrogen, as aforesaid, $C_1$-$C_{12}$ alkyl or $C_1$-$C_{10}$ cycloalkyl, $C_6$-$C_{16}$ aralkyl, phenyl optionally substituted with one, two or three chloro or $C_1$-$C_3$ alkyl. In general any pharmacologically acceptable cation may be used.

The biosynthesis of prostaglandin compounds and their pharmacological actions are technically complex and the details of the synthesis are not necessary for the practice of the present invention. However, in general terms, the immediate fatty acid precursors of prostaglandin biosynthesis are dihomo-y-linoleic acid (chemically known as 5,8,11-eicosatrienoic acid) and archidonic acid (chemically known as 5,8,11,14-eicosatetraenoic acid). Substantial quantities of these acids, which are primarily of dietary origin, may be synthesized in mammals from linoleic acid. The fatty acids are then stored as phospholipids. These phospholipids are then acted upon and released by the action of a phospholipase which is then the first step, and also rate limiting step, in the prostaglandin synthesis. The dihomo-y-linoleic acid is acted on by cyclooxygenase and this gives rise to prostaglandin E-1 through the endoperoxides PGG-1 and PGH-1.

Any carrier which is pharmaceutically acceptable and is pharmacologically inactive may be used to deliver the prostaglandin compound. Generally, dehydrated alcohols such as ethyl alcohol, normal propyl alcohol, isopropyl alcohol, etc. may be employed. Other carriers which may be employed are for example saline solutions. The amount of carrier used to deliver a given amount of prostaglandin is determined by the duration of the prostaglandin administration. Thus, if it is desired to administer the prostaglandin over a nine hour period, a determination of the amount of prostaglandin is made taking into consideration the patients weight, as hereinafter described. The amount of carrier selected will be sufficient to administer that determined amount of prostaglandin over the selected time period.

In use, the prostaglandin compound can be stored in unopened ampules and may be stable for up to two years in a refrigerated condition. When the prostaglandin compound is dissolved in a saline solution or glucose to form an infusion solution, this infusion solution can be stable for up to about 24 hours.

The prostaglandin is administered to the region in which an angioplasty procedure is to take place in an amount of about 25 nanograms to about 400 nanograms and preferably about 80 nanograms to about 260 nanograms and even more preferably in an amount of about 130 nanograms, based on prostaglandin E-1, for bolus injections. In some cases, it is desirable to intravenously administer the prostaglandin compound after the angioplasty procedure, as for example, generally continuously during a 12 hour period after the procedure, and which may vary somewhere between about 9 to about 15 hours. In this case, the prostaglandin compound is administered in an amount of about 10 to about 100 nanograms per kilogram of body weight per minute after the procedure, based on prostaglandin E-1, and during the 9 to 15 hour period.

More preferably, the prostaglandin compound is intravenously administered in an amount of about 15 to about 40 nanograms per kilogram of body weight per minute after the procedure, based on prostaglandin E-1, and during the 9 to 15 hour post angioplasty period. Here again, the amounts which are administered will vary from patient to patient, depending on those patient factors mentioned above, e.g. health, age, coronary health history, reaction to administration, etc.

The present invention also provides compositions which are effective for reducing dysfunction in angioplasty procedures and which involve the use of the prostaglandin compounds. The compositions generally comprise a carrier which contains a selected amount of the prostaglandin. The carrier must be one which does not alter the prostaglandin compound and does not inhibit its effectiveness. The carrier must also release the prostaglandin compound at a rate sufficient to dilate the blood vessels. Naturally, the carrier should be in a form which is capable of being intravenously introduced.

Each of the other prostaglandin compounds which are encompassed by the present invention have an efficacy directly related to that of prostaglandin E-1. Thus, the amounts of the other prostaglandin compounds which may be employed in the present invention is based upon the efficacy of prostaglandin E-1. For this purpose, the amount of any prostaglandin compound which is used in a carrier is present in an amount necessary to produce an efficacy approximately equivalent to the efficacy produced by at least a minimum of 25 nanograms of prostaglandin E-1 to the efficacy produced by a maximum amount of about 400 nanograms of prostaglandin E-1.

The efficacy which is produced by any other prostaglandin compound encompassed by the present invention can be easily related to the efficacy produced by prostaglandin E-1 based on trial techniques. In other words, it is relatively simple to determine the efficacy produced by using, for example, prostaglandin I-2 and to determine the efficacy produced by using prostaglandin E-1 such that the skilled artisan can easily determine the amounts of any other prostaglandin to be used based on the use of prostaglandin E-1. It should be understood that the efficacy which can be achieved by the prostaglandin compounds will naturally vary from patient to patient, although the beneficial results which have been achieved by use of the method and the compositions of the present invention are easily noticeable. Thus, the efficacy of a given prostaglandin compound cannot be precisely determined with respect to prostaglandin E-1, but is capable of being approximately equivalently determined taking into consideration the various divergences which will occur from patient to patient.

In the case of the prostaglandin I-2 compound, this prostaglandin compound would be present in the composition administered to the patient immediately before and immediately after the angioplasty procedure in a total amount of about 3.7 nanograms to about 75 nanograms. The prostaglandin I-2 more preferably would be administered in a range of about 12 nanograms to about 49 nanograms. The ciprostene prostaglandin compound would be present in the composition and administered to the patient immediately before and after the angioplasty procedure in a total amount of about 187 nanograms to about 6000 nanograms. The ciprostene prostaglandin preferably would be administered in a range of about 600 nanograms to about 3900 nanograms, and even more preferably about 1430 nanograms.

The above described quantities of prostaglandins are all based on the use of bolus injections. The amounts specified are also based on one intracoronary bolus injection prior to the angioplasty procedure and one bolus injection after the angioplasty procedure. Thus, each injection would be based on one-half the amounts specified. If intracoronary injections are made during the procedure, the amounts administered before and after would be altered. Further, the amounts administered may vary from patient to patient for the reasons mentioned above.

There are three general groups of carriers which have been found to be highly effective for use in the compositions of the invention. These carriers include isotonic solutions as well as two forms of hypertonic solutions. One type of hypertonic solution includes the angiographic contrast materials and the second form of hypertonic solution includes the biodegradable prostaglandin carrying spheres.

The isotonic solutions are generally all liquid in form and are typically various salt solutions. One of the preferred isotonic solutions is a saline solution present in an amount of about 5 cc. This amount of saline is effective to hold about 25 to about 400 nanograms of the prostaglandin E-1 compound. This amount of saline solution is also effective for generally all of the other prostaglandins encompassed by the present invention.

Other types of isotonic solutions which can be employed are 0.9 percent sodium chloride or some dextrose solutions, as for example a give percent (5%) dextrose solution. It is also possible to use a five percent (5%) dextrose solution with 0.2 percent sodium chloride therein. Lactated Ringers are also effective as one of the liquid carriers. The isotonic liquid carrier should have an osmolar strength about equivalent to that of seawater.

Angiographic contract material can also be used as an effective carrier for the prostaglandin compounds. Many of the angiographic materials which may be used are usually x-ray absorbent as for example, hypaque-sodium. Potassium iodine and certain other recognized potassium salts may also be used as the carrier solution. It is also possible to use multiple ionic materials such as potassium iodide and iron combinations as the carrier since they all function as angiographic contract materials.

The amount of the angiographic contract material which is employed depends upon the amounts which are normally used to achieve the necessary contract in an angiography procedure. Usually, about 3 cc to about 10 cc of the angiographic contrast material is used as the carrier per bolus injection.

The third group of carrier materials are the prostaglandin carrying microspheres. Generally, three major types of microspheres may be employed and these include: (1) protein laden microspheres, (2) carbohydrate laden microspheres and (3) free fatty acid laden microspheres.

The protein laden microspheres may include, for example, albumen laden microspheres. The carbohydrate laden microspheres may include, for example, various known and accepted starch laden microspheres as well as various known polysaccharides. Liposome is an effective example of a fat laden microsphere.

The term "microsphere" is used to represent particles ranging in size from about 7 u, the diameter of a red blood cell, to about 100 u in diameter. A particular group of "uniformly" sized microspheres may vary in diameter up to around 25%. Thus, a group of 10 u diameter microspheres might range in size from around 8.5 u to around 11.5 u in diameter. Usually, about 225,000 to about 500,000 microspheres are present as the carrier for a bolus injection.

The microspheres of the present invention may be composed of any long chain compound susceptible to cross linking to a solid in which amide or carboxyl groups are exposed or are capable of being exposed by suitable treatment. This includes, but is not limited to, latex materials such as polystyrene and styrene divinylbenzene, agarose, polyalkylcyanocrylate, albumin, cross-linked albumin, sucrose, starch, cellulose and dextran. Usually, about 225,000 to about 500,000 microspheres are present as the carrier for a bolus injection.

As indicated previously, the prostaglandin compound may be administered for a selected time period, as for example, nine to 15 hours after the angioplasty procedure. This intravenous administration, when coupled with the previously described intracoronary administration has been found to produce highly effective results. The amount of prostaglandin in the solution, which is administered drop-wise, should be in the range of about 10 nanograms to about 100 nanograms per kilogram of body weight per minute for prostaglandin E-1. Preferably, the prostaglandin E-1 is administered in a range of about 15 to about 40 nanograms per kilogram of body weight, per minute and even more preferably about 20 nanograms per kilogram of body weight per minute.

The amount of the other prostaglandin compounds which would be administered intravenously is also based on the efficacy of such other prostaglandins related directly to the efficacy of prostaglandin E-1. Thus, the prostaglandin in the carrier to be administered to a patient is present in an amount to deliver to the patient a desired weight of prostaglandin in nanograms per kilogram of body weight of the patient per minute to produce an efficacy equivalent to the efficacy of prostaglandin E-1 when administered in the selected range.

In a more preferred embodiment, the amount of prostaglandin E-1 is administered in a range of about 15 nanograms to about 40 nanograms per kilogram of body weight per minute, as aforesaid. With respect to the prostaglandin I.2 compound, this prostaglandin would be administered in an amount of about 1.5 nanograms to about 19 nanograms and preferably in a range of also 2 to about 7.5 nanograms per kilogram of body weight per minute. Ciprostene would be administered in an amount of about 75 nanograms to about 1500 nanograms and preferably about 112 to about 600 nanograms per kilogram of body weight per minute.

It has also been found in accordance with the present invention, that the intravenous administration of the prostaglandin compound followed by the intracoronary administration substantially reduces the restenosis which was normally encountered in angioplasty procedures. It may be observed from the following Example III that there was a marked decrease in restenosis when the intravenous administration of prostaglandin followed the intracoronary administration. In addition, when the amount of prostaglandin is reduced progressively to 0 during the last hour or two hours of the intravenous administration, there is a reduced tendency for the patient to suffer adverse effects.

The present invention is effective in providing compositions containing the above identified amounts of prostaglandin for ready administration of the same. Thus, and for example, a composition may contain a carrier and the amount of prostaglandin carried by that carrier which is necessary to produce an efficacy approximately equivalent to the efficacy produced by administration of prostaglandin E-1 in a range of about 25 nanograms to about 400 nanograms. More preferably, this composition would contain the prostaglandin compound necessary to produce an efficacy in a range approximately equivalent to the efficacy produced by the administration of 80 nanograms to about 260 nanograms of prostaglandin E-1.

The composition also preferably includes those carriers which were mentioned above and include those selected from the class consisting of (a) an isotonic solution, (b) an angiographic contrast material, and (c) biodegradable prostaglandin carrying microspheres.

In another embodiment, the composition of the present invention may be described as that composition which comprises the carrier for the prostaglandin compound and also the prostaglandin compound which is carried by that carrier. The prostaglandin is present so that it can administered over a selected time period at a relatively constant rate and in an amount to produce an efficacy approximately equivalent to that produced by the administration of prostaglandin E-1 in a range of about 10 nanograms to about 100 nanograms per kilogram of body weight per minute. In this way, the composition thereby provides the cyto-protection and the antithrombotic effects and the antiplatelet effects and the antispasmic effects.

The present invention also provides a kit or package containing the necessary components containing the prostaglandin compound in amounts to be administered in the proper dosage. Thus, a kit may be initially provided with a first syringe containing the amount of prostaglandin compound necessary to produce an efficacy produced by administration of 12 to about 200 nanograms of prostaglandin E-1 and preferably the efficacy produced by the administration of about 40 to about 130 nanograms of prostaglandin E-1. The kit would also contain a second syringe for a bolus injection and which would also contain a prostaglandin compound present in an amount to produce an efficacy approximately equivalent to the efficacy of about 12 nanograms to about 200 nanograms of prostaglandin E-1 and preferably an efficacy approximately equivalent to that produced by the administration of about 40 nanograms to about 130 nanograms of prostaglandin E-1. Finally, this kit or package would also include a container such as a sealed package containing the amount of prostaglandin compound necessary to provide intravenous administration for the selected time period of 9 to about 15 hours. Because the intravenous amount of prostaglandin to be administered is dependent on the body weight of the patient, the kit can include a chart (such as shown in the Table) cross-referencing an amount of prostaglandin to body weight to be admixed with a carrier solution, such as saline, to an administration amount of about 10 nanograms to about 100 nanograms per kilogram of body weight per minute over about a 12 to 18 hour period. Generally this intravenous administration is started at 10 ng/kg/min and then titrated down at six hours to 20 ng/kg/min for six hours, then down to 10 ng/kg/min for the last six hours. The kit may also contain instructions for preparing and administering the intracoronary and intravenous dosages of prostaglandin.

As a specific example of a package, the first syringe or container would contain about 65 nanograms of prostaglandin E-1 in a 1 cc saline solution and which may be diluted to about a 5 cc saline solution for use. The kit would also include a second syringe or container which contains about 65 nanograms of prostaglandin E-1 in 1 cc of a saline solution and which again may be diluted to about a 5 cc saline solution in use. Finally, the package or kit of the present invention would include, in this example, a container of the saline solution which administers about 15 to about 40 nanograms of prostaglandin E-1 per kilogram of body weight per minute for a 12 hour period.

EXAMPLES

The invention is further described by but not limited to the following examples.

EXAMPLE 1

In order to assess the effects of intracoronary prostaglandin E-1 on myocardial blood flow in relation to a successful coronary angioplasty, twelve patients were given sixty five nanograms of the prostaglandin E-1 which was hand injected by bolus under blinded conditions. The angioplasty procedure involved a residual luminal diameter of less than 40 percent. The sixty five nanograms prostaglandin E-1 was dissolved in about four milliliters of dehydrated alcohol. Twelve additional patients were given four milliliters of dehydrated alcohol as a placebo and control agent.

Digital radiographic assessments of contrast medium appearance time distal to the stenosed coronary artery under hyperemic conditions were made 45 seconds after the start of the angioplasty procedure. The same radiographic assessment was made as a control under non-hyperemic conditions on an intracoronary placebo 45 seconds after the start of the angioplasty procedure. This information was used to measure myocardial blood flow immediately before and after the administration of the prostaglandin E-1. The known accepted method of the reciprocal of the coronary flow ratio (CFR) was used to measure myocardial blood flow. Neither the prostaglandin E-1, nor the placebo elicited any angina, dysrythemia or any significant pressure changes.

This study revealed the following data in which PGE-1 is the prostaglandin E-1 compound and PTCA represents the percutaneous transluminal coronary angioplasty procedure. N represents the number of patients, MBF represents the myocardial blood flow and CFR represents the coronary flow ratio, LAD represents the left anterior descending coronary artery and RCA represents the right coronary artery.

| Parameter | | N | LAD or RCA Stenosis | CFR |
|---|---|---|---|---|
| IC Placebo | Pre-PTCA | 6 | 80.4 ± 11 | 1.02 ± 0.13]p = NS |
| IC PGE-1 | Pre-PTCA | 6 | 80.4 ± 11 | 1.14 ± 0.17 |
| IC Placebo | Post-PTCA | 6 | 24.6 ± 10 | 1.48 ± 0.14]p = .001 |
| IC PGE-1 | Post-PTCA | 6 | 24.6 ± 10 | 2.16 ± 0.34 |

EXAMPLE 2

In order to evaluate post angioplasty effects in which prostaglandin was administered, 40 patients were selected between the ages of 18 and 75. The patients were males or otherwise post-menopausal or sterilized females. The patients undergoing the post transluminal coronary angioplasty exhibited incapacitating angina or chronic stable angina while on maximal medical therapy.

Patient Selection and Grouping

Patients who had a cerebrovascular accident or acute myocardial infarction within two months prior to the test were excluded. Also excluded were patients having unstable ventricular arrhythemia refractory to conventional anti-arrhythemic therapy. Also excluded were any patients that had cancer within the past two years unless a complete cure was clinically evident for two years. Patients with streptokinase and patients with acute respiratory infections, or patients who had had surgery within several weeks preceding the test were also excluded. Further excluded were patients that had pericardial infusion and/or severe difuse pulmonary aveolar edema, patients with previous angioplasty vessel dilation, patients with coagulation disorders, active bleeding sites or gastrointestinal bleeding, or patients with poorly controlled diabetes mellitus.

The patients were divided into three groups which included a so-called "drug group", that is a group in which the patients were known to have received the prostaglandin E-1 compound, a so-called "open label" group in which the patients received either a placebo compound or otherwise the prostaglandin E-1 compound. The patients in this "open label" group received compositions handed to the physicians properly marked by a pharmacist, although the identification as to which patient in the "open label" group received the prostaglandin compound and which patient received a placebo was known only to the pharmacist and not to the physicians. Finally, the third group or so-called "placebo" group, received only a placebo composition which included only a dehydrated ethyl alcohol.

Nine patients were included in the placebo group, eight patients were included in the drug group and seven patients were in the open label group. The placebo group was comprised of six men and three women. There was one death within twenty four hours in postangioplasty, due to abrupt occlusion. Two of the patients in the placebo group did endure prolonged angina. In the drug group, patients were of a similar age having an average of fifty four years and was comprised of seven men and one woman. There were no abrupt occlusions, episodes of prolonged angina or any significant complications experienced in this group. Finally, in the open label group, five of the patients were men and two were women in a similar age range. No complications were exhibited in any patient in this postangioplasty group.

Procedural Steps

Prior to the insertion of the balloon catheter, all of the patients received 10,000 bolus units of heparin and intravenous nitroglycerine, as required, as well as sublingual nitrate and beta blockers or intravenous verapamil.

Prostaglandin E-1 was injected at sixty five nanograms intracoronary before and after the angioplasty procedures. Further, twenty nanograms per kilogram of body weight per minute were then infused into the patients over a twelve hour period, intravenously while monitoring the patients in an intensive care unit. The dosage was gradually tapered to 0 over the last six hours of this twelve hour period. The prostaglandin composition was infused through the balloon catheter into the myocardium at the time of prolonged balloon inflation.

The placebo composition was administered to the patients in the placebo group much in the same manner as the prostaglandin E-1 was administered to the patients in the drug group. Finally, the proper composition known by the pharmacist was administered to each of the patients in the open label group. In the case of those patients in the drug group, during inflation and total occlusion, the prostaglandin composition infusion occurred intravenously in the dosage specified.

Thereafter, a 2D echocardiogram was placed over the heart during the occlusion and an LV function change was measured simultaneously. Further, alpha platelet IV as well as beta thromboglobulin was measured immediately and fifteen minutes after balloon inflation.

The 2D echocardiogram was re-measured at three and six month intervals after the angioplasty procedure in order to determine the effects of the prostaglandin composition and the angioplasty procedure itself on left ventrical function, both globally and regionally. Also, duration of reactive hypermia was measured after balloon inflation along with a gradient as an approximation of coronary blood flow.

Method of Measuring Coronary Blood Flow

The method of Vogel, et al. was used to measure coronary blood flow (Application of Digital Techniques to Selective Coronary Arteriography. Use of Myocardial Contrast Appearance to Measure Coronary Flow Reserve. American Heart Journal, Volume CVII, Number 1, January 1984).

The prostaglandin compound is used as a hypermia inducing substance, instead of being used for contrast. Beyond that, the method and equipment are identical. Digital processing of the 35 mm. cine films was digitized. Gated interval differencing and functional image generation were employed in accordance with the method of Vogel. The digital images were stored in a disk memory and subsequent processing was performed on a mini computer.

A single intensity and color modulated functional image is generated in five colors. Each corresponds to one of the five postcontrast or prostaglandin injection cardiac cycles analyzed and are used to display the cycle in which contrast medium appeared in each pixel.

In accordance with the technique described by Vogel, supra, 256 intensity levels were used to depict the relative amount of the increase in contrast medium that occurred in each pixel during its appearance in a cycle. This form of dual-function arteriographic image has been termed "contrast medium appearance picture". This is coupled with the myocardial contrast appearance time, i.e., the time from the onset of contrast injection to its appearance within the region of myocardium, and this was then used as an index of regional coronary blood flow.

In order to measure intracoronary blood flow before and after prostaglandin administration, digital radiographic assessment of contrast medium appearance time distal to the targeted stenosed coronary artery was used. Measurements were made for prostaglandin P-1 under hyperemic conditions, i.e., 65 nanograms of intracoronary prostaglandin E-1 after 45 seconds, versus a control, and nonhyperemic conditions, i.e., intracoronary placebo (5 cc of absolute alcohol), to measure myocardial blood flow before and immediately after the coronary angioplasty. The accepted method of the reciprocal of the coronary flow ration was used to determine myocardial blood blow, substituting, however, intracoronary prostaglandin E-1 for contrast as the hyperemia inducing agent. Neither the intracoronary prostaglandin E-1 nor placebo elicited any angina, dysrhythmia, or significant pressure changes. Equivalent dosages for other intracoronary E-1 like prostaglandins are also employed, based on the compound's potency as compared to intracoronary prostaglandin E-1. The intravenous route is preferred for intracoronary prostaglandin E-1 like prostaglandin compounds (including PGE-12, its salts, esters, and amids). However, other systemic routs of administration (e.g. oral, parenteral, intra-arterial) may also be employed as long as the dosage used achieves the same blood level of drug as the intravenous route.

As summarized by Vogel in The Radiographic Assessment of Coronary Blood Flow Parameters. Circulation, Vol. LXXII, No. 3, September 1985, this imaging technique to measure coronary blood flow is performed rapidly during cardiac catheterization. However, atrial pacing, PCG synchronized power injection of contrast media, digital radiographic equipment capable of direct digital storage and fixed patient positioning were added to the routine technique and did not result in any problems.

Results

Seventeen doubly blinded patients did provide data which allowed for complete analysis. Nine patients were given the placebo hand-injected, bolus, intracoronary before and after the angioplasty procedure, and the myocardial blood flow was measured as described above.

Under double blinded conditions, the placebo given was the 4 or 5 cc. of dehydrated alcohol, and this same vehicle was used for the prostaglandin E-1. In this group of nine, there was one death in 24 hours and two episodes of prolonged angina documented by ECG change. This did not appear in the patients given the 65 nanograms of intracoronary prostaglandin E-1 hand-injected, bolus, in the double blinded drug group.

The percent stenosis of the target vessel in the placebo and drug groups were similar, being 80 percent mean pre-angioplasty and 25 percent mean post-angioplasty, as measured by standard visual criteria. The patients receiving the drug in the open label group had similar degrees of stenosis in their coronary arteries prior to angioplasty. The incidence of unstable angina, antecedent myocardial infarction, or post-infarction angina, was similar in all three groups, namely, 33 percent in the placebo group, 25 percent in the drug group, and 29 percent in the open label group, regarding myocardial infarction, one patient with unstable angina post-infarction in the drug group, none in the placebo group, and two in the open label group.

When comparing the placebo group with the intracoronary drug group, the nine patients receiving the intracoronary placebo injection, pre-coronary angioplasty, showed a reciprocal of the coronary flow ratio of $1.04 \pm 0.13$ standard error of the mean. Eight patients in the drug group, pre-coronary angioplasty, and the seven patients in the open label group, pre-coronary angioplasty, showed a coronary flow ratio of $11 \pm 0.17$, and the difference between the placebo and drug group was not significant pre-angioplsty. It should be noted that despite the tight flow limiting stenosis in the ascending coronary arteries, intracoronary prostaglandin E-1 did augment flow slightly, but this was not significant because of the flow limiting stenosis.

The nine patients in the placebo group, post-angioplasty, had a coronary flow ratio of $1.54 \pm 12$, which is higher than the precoronary angioplasty flow. In the drug group and the open label group, the coronary angioplasty flow. In the drug group and the open label group, the coronary angioplasty elicited an intense hyperemia, which yielded a coronary flow value of $2.31 \pm 0.34$ with the P-value of points less than 0.001 using a student two tailed T-test. In the open label group, the duration of the hyperemia was tested with two and five minute repetitions of the coronary flow value and the hyperemia was still much above a baseline flow. In two patients in the open label group, the comparison of the hyperemic response of intracoronary prostaglandin E-1 was 22 percent higher than judged by the coronary flow value.

Two-dimensional echocardiography was performed immediately after the angioplasty and repeated at least once within two days prior to the patient beling dis-changed, i.e. whenever clinically feasible. The echocardiography did show, in the placebo group, no significant increase in regional ventricular function. In the doubly blinded drug group, three of eight patients did show increase in regional function as judged by independent analysis by a blinded investigator, via 2D echocardiographic criteria. In the open label group, two of seven patients did show dramatic increase in regional LV function. However, one patient did have unstable angina prior to the angioplasty.

Conclusion

Based on the foregoing analysis, it was concluded that the intracoronary prostaglandin E-1 and the intravenous prostaglandin E-1 in the above described dosages was safe and created no serious side effects. Moreover, the prostaglandin compounds, when used as described herein, elicit an intense hyperemia, at least doubling coronary blood flow directly. This effect appears to be prolonged without inducing any hemodynamic complications, such as hypotension.

The vasodilating and hyperemic effects of prostaglandin E-1 appears to be a direct result of its antispasm effect in the area where the plaque is ruptured by balloon dilation. Angiography reveals that there appears to be, in almost all instances of angioplasty, a subintimal disruption and which is the technique by which the plaque is fractured during the angioplasty procedure and hence the flow obstruction removed.

Thus, it was concluded that in unstable angina the prostaglandin E-1 and the other prostaglandin compounds do inhibit platelet aggregation at the site of antheroma fracturing during angioplasty. Consequently, embolization of microemboli platelets in a downstream position is not noted. As a result, and as could be anticipated, prolonged angina or abrupt closure was not observed in the drug group, as it was observed in the placebo group.

It was postulated that it is really impossible to determine the appearance and condition of coronary vessels in a post-angioplasty procedure condition by angiographic criteria. Under pathologic studies previously performed, and under angioscopy, a roughing and tearing of the intima and media is almost always observed. Consequently, the angiogram therefore underestimates the amount of damage to a vessel which is subjected to an angioplasty procedure. The site of the procedure is unable to synthesize local prostaglandins. Thus, the thromboxane that is released by the platelets is unopposed which results in spasm or thrombus. The exogenous prostaglandin E-1 and the other prostaglandin compounds encompassed by the present invention delivered in sufficient dosages in accordance with the present invention clearly overcomes these effects.

It was also concluded that the hyperemic or increased blood flow state induced by the intracoronary prostaglandin was prolonged more than with intravenous nitroglycerine. Thus, it was also concluded that it is desirable, in most cases, to continue the intravenous prostaglandin E-1 for at least 12 hours post-angioplasty and postintracoronary injection to obtain the most beneficial effects of the prostaglandin compound.

Based on the foregoing, it was concluded that the prostaglandin compound exhibits substantial antithrombotic and antiplatelet effects, as abrupt occlusion and thrombosis were not observed in the drug group, but were observed in the placebo group. The prostaglandin compound does exhibit a myosite protection effect, both cellular and as an inhibitor of platelet aggregation.

EXAMPLE 3

Forty patients were evaluated in a double blind study in order to determine whether an intravenous infusion of prostaglandin E-1 produced the desired salutary effects after a coronary angioplasty procedure. Twenty to forty nanograms per kilogram per minute of prostaglandin E-1 (test patients) versus a normal saline placebo (placebo patients) was infused into certain of the test patients for a period of twelve hours after the angioplasty procedure. Further, one hundred and thirty nanograms bolus of prostaglandin E-1 was administered in an intracoronary procedure during the angioplasty procedure. All of the patients were prepared prior to angioplasty in accordance with the typical procedures with aspirin, dipyridamole, heparin, nitrites and nifedipine and/or verapamil. Moreover, administration of these latter drugs continued after the angioplasty procedure.

The prostaglandin E-1 produced a reduction in a number of episodes of abrupt occulsions with three occuring in eighteen patients which did not receive the prostaglandin E-1 and none in fourteen patients which did receive the prostaglandin E-1. All patients with disection and/or long spasm had repeat angiograms within seven days. With disection during the angioplasty procedure, prostaglandin E-1 inhibited prolonged spasms (2/5 for those patients not receiving the prostaglandin and 0/6 for those patients receiving the prostaglandin) and restenosis despite systemic heparinization for two to seven days after the angioplasty procedure (2/2 for patients not receiving the prostaglandin E-1 versus 0/6 for patients receiving the prostaglandin E-1).

Adverse effects of prostaglandin E-1 infusion at this stage did not occur, primarily because the patients were deliberately volume overloaded. In conclusion, it was determined that a prostaglandin E-1 injection intracoronary followed by intravenous infusion in patients undergoing the angioplasty procedure is quite safe. Prostaglandin E-1 appears to inhibit coronary spasms and abrupt occulsion, particularly when disection is produced by the angioplasty procedure. This salutory clinical effect of prostaglandin E-1 occurs in addition to the effects of standard pharmaceutical agents currently used in angioplasty procedures.

One of the unique results which has been found in connection with the present invention is a very substantial reduction in restenosis, as is evident by the foregoing Example 3. The problem of restenosis in connection with angioplasty procedure is one which has plagued cardiologists for a long period of time. Moreover, little is known about the causes of restenosis. Nevertheless, it has been observed that there is a very substantial decrease in restenosis when the prostaglandin compound is administered in the ranges described herein.

More specifically, it has been found that the restenosis is decreased substantially as a result of the intra-arterial administration immediately before and/or immediately after the angioplasty procedure and which is followed by the intravenous administration of the prostaglandin, as described above. In the forty cases tested, as in Example 3, only five of the patients demonstrated early restenosis and all five patients were in the placebo group. In other words, all patients whom received the prostaglandin compound in accordance with the procedure specified herein suffered no early restenosis. It is preferred to use the same prostaglandin compound for the intravenous administration as was used for the intra-arterial administration, although this is not absolutely necessary.

Although it is not certain, it is theorized that the postangioplasty procedure intravenous infusion in combination with the intracoronary administration leads to the significant results and substantial reduction of restenosis. It is believed that the infusion during the last nine to fifteen hours and preferably the last twelve hours affects the platelet deposition and platelet aggregation. Thus, by reducing the platelet deposition and aggregation, previously encountered problems of early restenosis have been reduced, if not fully eliminated.

It will be appreciated therefor, from the foregoing description, that the present invention represents a significant advance in the reduction of dysfunction resulting from angioplasty procedures and particularly from myocardial angioplasty procedures. In particular, the invention provides a kit and method for administering a prostaglandin compound in a desired amount in order to provide cyto protection and to provide antithrombotic effects, antiplatelet effects and antispasmic effects. In general, the prostaglandin, when administered in the proper amounts, also aids in the dilation of the artery.

TABLE

| DOSAGE (ng/kg/min) | Dosage Calculation Nomogram (4000 ng/ml) Rate in ml/hr | | | | | | | | | | | | | | |
|---|---|---|---|---|---|---|---|---|---|---|---|---|---|---|---|
| | WEIGHT (KG) | | | | | | | | | | | | | | |
| | 40 | 45 | 50 | 55 | 60 | 65 | 70 | 75 | 80 | 85 | 90 | 95 | 100 | 105 | 110 |
| 40 | 24 | 27 | 30 | 33 | 36 | 39 | 42 | 45 | 48 | 51 | 54 | 57 | 60 | 63 | 66 |
| 20 | 12 | 14 | 15 | 17 | 18 | 20 | 21 | 23 | 24 | 26 | 27 | 29 | 30 | 32 | 33 |
| 10 | 6 | 7 | 8 | 9 | 9 | 10 | 11 | 12 | 12 | 13 | 14 | 15 | 15 | 16 | 17 |

Dosage calculated as follows:

$$\text{Rate (ml/hr)} = \frac{\text{wt(kg)} \times \text{Dose (mg/kg/min)} \times 60}{4000 \text{ mg/ml}}$$

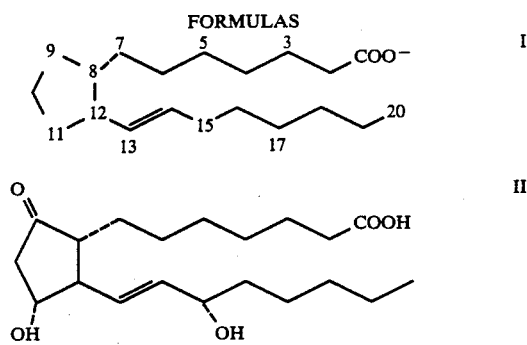

FORMULAS

-continued
FORMULAS

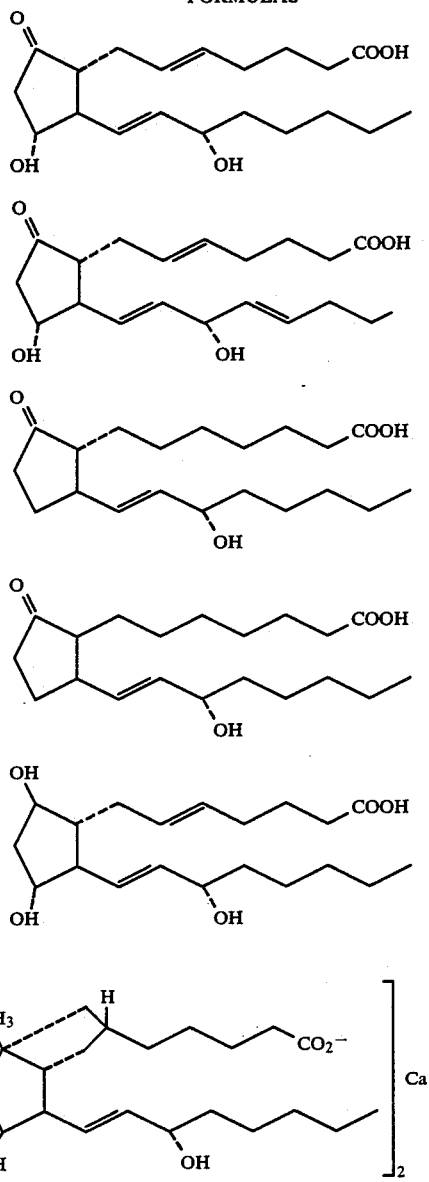

We claim:

1. A kit containing a combination of components for preventing or treating arterial dysfunction resulting from angioplasty procedures, said kit containing:
   (a) a first container comprising about 25 to about 200 nanograms of a prostaglandin $E_1$ or a prostaglandin pharmacologically equivalent thereto for bolus injection into an artery of a patient;
   (b) a second container comprising a prostaglandin $E_1$ or a prostaglandin pharmacologically equivalent thereto for intravenous administration after said bolus injection sufficient to provide 10 to about 100 nanograms per kilogram of body weight per minute over at least a 6 hour period;
   (c) a chart cross-referencing an amount of said prostaglandin from said second container to body weights to be admixed with a saline solution to prepare a dosage amount of about 10 nanograms to about 100 nanograms per kilogram of body weight per minute.

2. The kit of claim 1 which additionally includes a sealed package of saline solution for preparing said intravenous administration.

3. The kit of claim 1 wherein said first and/or second container are syringes containing said prostaglandin.

4. The kit of claim 1 wherein said first container contains about 40 to about 130 nanograms of said prostaglandin.

5. The kit of claim 4 wherein said first container contains about 65 nanograms of said prostaglandin in a 1 cc solution.

6. The kit of claim 1 which additionally includes a third container comprising about 25 to about 200 nanograms of said prostaglandin for injection into said artery after an angioplasty procedure.

7. The kit of claim 6 wherein said third container contains about 40 to about 130 nanograms of said prostaglandin.

8. The kit of claim 7 wherein said third container contains about 65 nanograms of said prostaglandin in a 1 cc solution.

9. The kit of claim 1 wherein said second container is a container of saline solution containing an amount of said prostaglandin to provide a 15 to about 40 nanograms of prostaglandin per kilogram of body weight per minute.

10. The kit of claim 1 wherein said prostaglandin in each of said containers is present in a carrier comprising:
    (a) an isotonic solution;
    (b) an angiographic contrast material;
    (c) a biodegradable prostaglandin carrying microsphere; or
    (d) a combination thereof.

11. The kit of claim 10 wherein said microspheres comprise:
    (a) albumen laden microspheres;
    (b) carbohydrate laden microspheres; or
    (c) free fatty acid laden microspheres.

12. The kit of claim 10 wherein said carrier comprises:
    (a) an isotonic solution which is present in a 5 cc amount;
    (b) an angiographic contrast material present in an amount of about 3 cc to about 10 cc per bolus; or
    (c) biodegradable prostaglandin carrying microspheres having sizes within the range of about 10 microns to about 100 microns and which are present in an amount of about 225,000 to about 500,000.

13. The kit of claim 6 wherein said prostaglandin is present in a carrier comprising:
    (a) an isotonic solution;
    (b) an angiographic contrast material;
    (c) a biodegradable prostaglandin carrying microsphere; or
    (d) a combination thereof.

14. The kit of claim 13 wherein said microspheres comprise:
    (a) albumen laden microspheres;
    (b) carbohydrate laden microspheres; or
    (c) free fatty acid laden microspheres.

15. The kit of claim 13 wherein said carrier comprises:
    (a) an isotonic solution which is present in a 5 cc amount;
    (b) an angiographic contrast material present in an amount of about 3 cc to about 10 cc per bolus; or
    (c) biodegradable prostaglandin carrying microspheres having sizes within the range of about 10 microns to about 100 microns and which are present in an amount of about 225,000 to about 500,000.

* * * * *